United States Patent
Reddy et al.

(10) Patent No.: US 6,294,064 B1
(45) Date of Patent: *Sep. 25, 2001

(54) METHOD AND REAGENT FOR SUPPRESSING THE INJECTION OF NUCLEIC ACID SEQUENCING TEMPLATE INTO MICRO-BORE CAPILLARY DURING DNA SEPARATION WITH CAPILLARY ELECTROPHORESIS

(75) Inventors: M. Parameswara Reddy, Orange; Tung-Liang Huang, Placentia; Chitra K. Ratnayake, Yorba Linda; Daniel A. Keys, Irvine, all of CA (US)

(73) Assignee: Beckman Coulter, Inc., Fullerton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/447,386

(22) Filed: Nov. 23, 1999

(51) Int. Cl.[7] .............. B01D 51/02; B01D 59/42; G01N 33/00; C07H 21/04; C12P 19/34
(52) U.S. Cl. ............ 204/451; 204/450; 204/456; 204/483; 436/94; 536/23.1; 435/91.1
(58) Field of Search ............ 435/6, 91.1; 436/94, 436/501; 702/20; 204/450, 451, 453, 454, 456, 466, 467, 469; 422/50

(56) References Cited

U.S. PATENT DOCUMENTS 5,891,313 * 4/1999 John et al. .................. 204/451
5,994,057 * 11/1999 Mansfield .................... 435/6

OTHER PUBLICATIONS

"Principles of Polymerization", George Odian, 3rd Edition, p. 17, John Wiley & Sons, Inc., 1991.

Technical Information #T–1854A, Beckman Coulter, Inc. 1998, "CEQ 2000 DNA Analysis System Performance", Nora M. Galvin et al.

Template Suppression reagent, part #401674, The Perkin–Elmer corp., Foster City, CA.

Braun et al., Capillary electrophoresis of DNA restriction fragments: effect of polymer properties. Electrophoresis 18, 1994–1997, 1994.*

* cited by examiner

Primary Examiner—Ethan Whisenant
Assistant Examiner—Frank Lu
(74) Attorney, Agent, or Firm—William H. May; Arnold Grant

(57) ABSTRACT

Reagents and methods for preparing samples containing both biomolecule analytes and macrobiomolecules for capillary electrophoresis separation are provided. The reagents comprise a branched polymer. When mixed with a sample containing both biomolecule analytes and macrobiomolecules, particularly DNA templates, the branched polymer of the reagent can suppress the entrance of the macrobiomolecules into a capillary electrophoresis tube during electrokinetic injection of the sample into the capillary electrophoresis tube.

31 Claims, 2 Drawing Sheets

METHOD AND REAGENT FOR SUPPRESSING THE INJECTION OF NUCLEIC ACID SEQUENCING TEMPLATE INTO MICRO-BORE CAPILLARY DURING DNA SEPARATION WITH CAPILLARY ELECTROPHORESIS

BACKGROUND OF THE INVENTION

1. Area of the Art

The invention relates generally to capillary electrophoresis of biomolecule analytes, and specifically to methods and reagents for preparing nucleic acid samples for nucleic acid separation with capillary electrophoresis.

2. Description of the Prior Art

Throughout this application various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Capillary electrophoresis (CE) is a technique that has been used to separate proteins or nucleic acids such as DNAs from each other. See, for example, Chen, Fu-Tai A. et al., "Capillary Electrophoresis—A New Clinical Tool," *Clin. Chem.* 77/1:14–19 (1991); see, also, U.S. Pat. Nos. 5,120,413 and 5,228,960; see, further, U.S. Pat. No. 5,891,313. These documents are incorporated herein by reference.

In general, CE involves introduction of a sample into a capillary tube, i.e., a tube having an internal diameter of from about 2 to about 2000 microns, and the application of an electric field to the tube. The electric potential of the field both pulls the sample through the tube and separates it into its constituent parts. Each of the sample constituents has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

The results of CE analysis are typically presented as "electropherograms", i.e., peaks of various widths and heights which correspond to the constituent parts of the sample. For example, a constituent which is present in a sample in a high concentration may evidence a peak having a large height and wide width compared to a constituent present in a (relatively) low concentration. Typically, the electropherogram is derived by plotting detection units (typically ultraviolet light absorbance) on the vertical axis, and time of constituent traversal through the column to a detection region on the horizontal axis. Results can also be derived in terms of a unit value, typically derived from the peak areas or peak heights.

Electrokinetic loading of a DNA sequencing sample mixture into a capillary electrophoresis tube is a preferred method of introducing a sample of analytes into the capillary electrophoreisis tube. However, DNA sequencing product primarily contains a mixture of labeled DNA sequencing fragments, whose separation and analysis provide sequencing information, and larger DNA template. Therefore, during the electrokinetic injection of the DNA sequencing fragments, the amount of analyte introduced into the capillary is limited by the buildup of nucleic acid template at the injection end of the capillary. This template buildup clogs the end of the capillary and inhibits passage of analyte into the capillary. This phenomenon limits the amount of DNA fragments that can be injected and electrophoresed. In addition, the injection of the large DNA template into a narrow bore capillary is known to reduce the local conductivity of the medium inside the capillary, leading to high electrical resistance and local Joule heat. High Joule heat would deteriorate the separation resolution and generate bubbles inside the capillary. The latter case actually produces a severe current problem with the electrophoretic separation. It is therefore desirable to have a suitable way to suppress the DNA templates entering the capillary to reduce the above-mentioned problems.

Some strategies to solve or remedy the template-clogging issue are: a) thorough purification of sample to remove the template; and b) cutting off the template-clogged end of the capillary end shortly after introduction of the sample. These methods are either time-consuming, inconvenient and/or expensive. None of them are ideal for supporting the high-speed and high-throughput systems as required by the human genome project.

Another known approach to suppress the entrance of nucleic acid sequencing template into the capillary is to dissolve the template-containing sample in a loading solution consisting of linear polymer and denaturant.[1,2] The function of the linear polymer is to trap the nucleic acid template to inhibit the entrance of template into the capillary during the sample injection course. While this method is simple and easy, it is found that with this approach, the linear polymer significantly suppresses the mobility of the analyte DNA into the capillary, leading to low sample loading and thus low detection signal. Thus, a need exists to develop a new method that suppresses the entrance of nucleic acid sequencing template into the capillary without compromising the sample loading and detection signal.

SUMMARY OF THE INVENTION

It is an object of the present invention to provide methods and reagents that suppress the entrance of nucleic acid sequencing template into the capillary. It is also an object of the present invention to provide methods and reagents that improve the sample loading efficiency, capillary separation resolution, and detection sensitivity during nucleic acid separations with capillary electrophoresis.

These and other objects and advantages are achieved by the reagents and methods of the present invention. One aspect of the present invention provides a sample loading reagent for loading biomolecule analytes contained in a sample into a capillary electrophoresis tube. The reagent comprises a branched polymer and a solvent. The branched polymer, such as branched polyvinylpyrrolidone, may be dissolved in a solvent such as formamide to form a reagent that can suppress the entrance of macromolecules contained in a sample into a capillary electrophoresis tube during electrokinetic injection of the sample into the tube.

Another aspect of the present invention also provides a method for preparing a sample containing biomolecule analytes and macrobiomolecules for capillary electrophoretic separation of the biomolecule analytes. The method comprises the steps of:

(a) providing a reagent comprising a branched polymer; and (b) mixing the sample with an amount of the reagent sufficient to suppress the injection of the macrobiomolecules contained in the sample into a capillary electrophoresis tube during electrokinetic injection of the biomolecule analytes.

A further aspect of the present invention provides a method of loading biomolecule analytes into a capillary electrophoresis tube from a sample containing the biomolecule analytes and macrobiomolecules. The method comprises the steps of:

(a) providing a reagent comprising a branched polymer;
(a) mixing the sample with an amount of the reagent to form a mixture;
(b) electrokinetically injecting a portion of the mixture into a capillary electrophoresis tube;
wherein the amount of the reagent is sufficient to suppress the injection of the macrobiomolecules into the capillary electrophoresis tube.

In accordance with embodiments of the present invention, the biomolecule analytes may be DNA sequencing fragments, and the macromolecules may be DNA sequencing templates. The branched polymers may be branched polyvinylpyrrolidone, which may be dissolved in a solvent such as formamide.

The reagents and methods of the present invention provide a number of advantages. They can effectively suppress the entrance of nucleic acid sequencing template into the separation capillary, resulting in stable and reliable electrophoretic separation for DNA analysis. Compared to the commercial loading buffer comprising linear polymers, the reagents and methods of the present invention have demonstrated a better capability of differentiating the large-sized DNA template from the analyte, such that the detection signal with the analyte is not reduced as much as with the loading solution of linear polymer. In addition, compared to other known methods, e.g., post-sequencing purification, etc., for solving the template-clogging issues, the disclosed method is fast and simple.

The reagents and methods of the present invention are well-suited for use in any capillary electrophoretic separation, particularly for DNA-related applications like sequencing and fragment analysis. The reagents and methods of the present invention may be used in connection with a capillary electrophoresis system such as, but not limited to, CEQ™ 2000 DNA Analysis System, P/ACE™ MDQ Capillary Electrophoresis System and Paragon CZE® 2000 Capillary Electrophoresis System, which are commercially available from Beckman Coulter, Inc., Fullerton, Calif., USA.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1A:
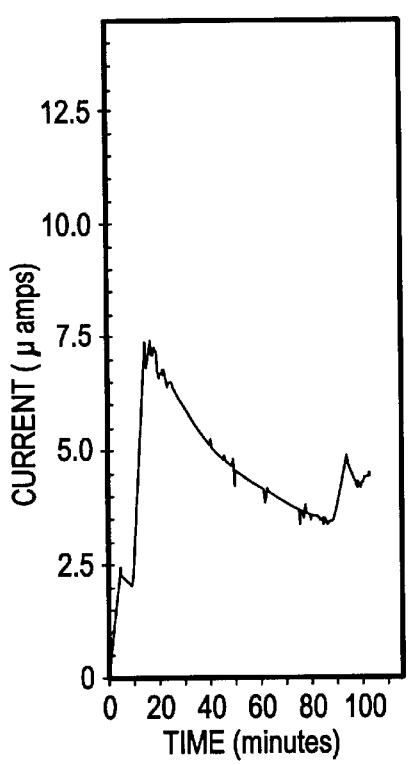
FIGS. 1(a) to 1(c) are current profiles of DNA sequencing separations with the CEQ 2000 DNA Analysis System.

The present invention provides reagents and methods for preparing a sample containing biomolecule analytes and macrobiomolecules for capillary electrophoretic separation of the biomolecule analytes. Typically, a reagent of the present invention comprises a branched polymer. When a sample of the present invention is mixed with a reagent of the present invention, the branched polymer will suppress the injection of the macrobiomolecules contained in the sample into a capillary electrophoresis tube during electrokinetic injection of the biomolecule analytes contained in the sample into the capillary electrophoresis tube.

The term "macrobiomolecules" as used herein includes proteins, nucleic acids, genomic DNA, nucleic acid sequencing templates, PCR products, and the like. Generally, a macrobiomolecule of the present invention has a molecular weight of at least about 0.3 million daltons. In accordance with one embodiment of the present invention, the macrobiomolecules are DNA sequencing templates. In this case, the templates have at least 1,000 bases, and have a molecular weight of at least about 0.3 million. The biomolecule analytes can be DNA or RNA fragments, but typically are DNA fragments, particularly DNA sequencing fragments, having a length of about 20 to 1,000 bases and a molecular weight range of about 6,000 to 300,000 daltons. A sample containing the biomolecule analytes and macromolecules may be in a solid form or a liquid form, such as a liquid nucleic acid sequencing sample mixture.

For the purpose of the present invention, a branched polymer may be any branched polymer defined as "that are those in which there are side branches of linked monomer molecules protruding from various center branch points along the main polymer chain."[3] Examples of branched polymers of the present invention include, but are not limited to, branched polyvinylpyrrolidone, and the homopolymer or copolymers of vinyl pyrrolidone, acrylamide and its derivatives, ethylene glycol, ethylene oxide, vinyl alcohol, celluloses and its derivatives, dextrans and its derivatives, and mixtures of the above polymers. In accordance with one embodiment of the present invention, a branched polymer is branched polyvinylpyrrolidone. Preferably, the molecular weight of the branched polymer is in a range of about 1,200,000 to 2,000,000 dalton.

A reagent of the present invention may include a solvent. Typically, a branched polymer of the present invention is dissolved in the solvent. A branched polymer of the present invention may be dissolved in any solvent that fulfills the following criteria:
i) The solvent is not reactive to the dissolved branched polymer.
ii) The solubility of branched polymer in the selected solvent shall be at least 0.1% ( w/v), and preferably about 1.5%.
iii) DNA molecules should be soluble in the solvent.

Examples of the solvent that may be used in the present invention include, but are not limited to, formamide, water, low ionic aqueous solutions, mixture of formamide and aqueous solution mixture of the above containing other denaturants like urea, and mixture of the above with non-aqueous solvents such as methanol, ethanol and DMSO.

In one embodiment of the present invention, the solvent is formamide. Typically, when a branched polymer is dissolved in a solvent, its concentration is in a range of about 0.5 to 5% (w/v).

In preparing a sample for capillary electrophoretic separation, the sample is dissolved in or mixed with an amount of a reagent of the present invention. The amount of the reagent of the present invention must contain a sufficient amount of branched polymer such that, during electrokinetic injection of the sample to the capillary electrophoresis tube, the injection of macromolecules contained in the sample is suppressed. It is to be understood that the amount of the reagent may vary depending on the type of macromolecule, and amount of macromolecules, that are contained in a sample, and the determination of the necessary amount is well within the skill of one in the art in view of the disclosure of the present invention. In accordance with one embodiment, 1.875% (w/v) of branched polymer solution is applicable to a wide concentration range of 5–1,000 fmole of typical DNA templates.

Before mixing a sample with a reagent of the present invention, a sample may be pre-treated. For example, a DNA sequencing template may be preheated under a condition that will nick or linearize the DNA sequencing templates contained in the sample. In accordance with one embodiment, a DNA sequencing template may be preheated at a temperature of above 80° C. for at least one minute. Preferably, the DNA sequencing template is preheated at a temperature of about 80° C. to 100° C. for about one to three minutes.

A sample prepared in accordance with the present invention may be directly loaded into a capillary electrophoresis tube by electrokinetic injection for capillary electrophoretic separation. Accordingly, the present invention also provides a method of loading biomolecule analytes into a capillary electrophoresis tube from a sample containing the biomolecule analytes and macrobiomolecules. The method includes the steps of:

(a) providing a reagent comprising a branched polymer;

(a) mixing the sample with an amount of the reagent to form a mixture;

(b) electrokinetically injecting a portion of the mixture into a capillary electrophoresis tube, wherein the amount of the reagent is sufficient to suppress the injection of the macrobiomolecules into the capillary electrophoresis tube.

The sample prepared in accordance with the present invention may be used in connection with any capillary electrophoresis system suitable for separating biomolecule analytes contained in a sample, particularly for DNA-related applications like sequencing and fragment analysis. The reagents and methods of the present invention may be used in connection with a capillary electrophosis system such as, but not limited to, CEQ 2000, P/ACE MDQ and Paragon CZE 1000.

In accordance with the present invention, a sample prepared in accordance with the methods of the present invention may be loaded into a capillary tube by electrokinetic injection. During the sample injection, the branched polymer of the present invention can suppress the entrance of the macromolecules such as DNA sequencing templates into the capillary tube, while allowing the biomolecule analytes contained in the sample to be injected to the capillary tube. Electrokinetic injection of a sample into a capillary tube for capillary electrophoresis is well known in the art, and will not be repeated herein for simplicity. A general description of the electrokinetic injection method for DNA sequencing separation can be found in the literature.[4]

The reagents and methods of the present invention provide a number of advantages. They can effectively suppress the entrance of nucleic acid sequencing template into the separation capillary, resulting in stable and reliable electrophoretic separation for DNA analysis. Compared to the commercial loading buffer comprising linear polymers, the reagents and methods of the present invention have demonstrated better capability of differentiating the large-sized DNA template from the analyte, such that the detection signal with the analyte is not reduced as much as with the loading solution of linear polymer. In addition, compared to other known methods, i.e., post-sequencing purification, etc., for solving the template-clogging issues, the disclosed method is fast and simple.

The following examples illustrate various preparations and methods employed in practicing the present invention. The examples are meant to illustrate, but not to limit, the scope of the invention. Indeed, those of ordinary skill in the art can readily envision and produce further embodiments, based on the teachings herein, without undue experimentation.

EXAMPLE I

DNA Sequencing Separations with CEQ 2000 DNA Analysis System Utilizing Different Sample Loading Reagents Preparation of the loading reagent of the present invention: branched polyvinylpyrrolidone (PVP) (commercially available from BASF, Mount Olive, N.J., USA), with weight-average molecular weight of 1.2 to 2 million Da, was dissolved (0.5–5% w/v) in formamide by continuously stirring the polymer at 4–5° C. for approximately 16 hours. The resulting solution was then used for DNA sample loading for capillary electrophoretic separation.

DNA sample preparation and capillary electrophoretic separation: DNA sequencing fragments of a 3.5 kb plasmid containing Mouse Glucokinase insert (G2) (200 fmole) labeled with four cyanine-dye terminators were reconstitued in 40 µL of one of the following loading solutions before injection: a) formamide, b) the disclosed branched polyvinylpyrrolidone solution in formamide (1.875% w/v), and c) the commercial loading solution with linear polymer (commercially available through Perkin-Elmer Corp., Foster City, Calif. USA).

The separation conditions are 8.2 kV at 45° C. for 104 min. with 50-cm separation length (53-cm total length).

Figure 1B:
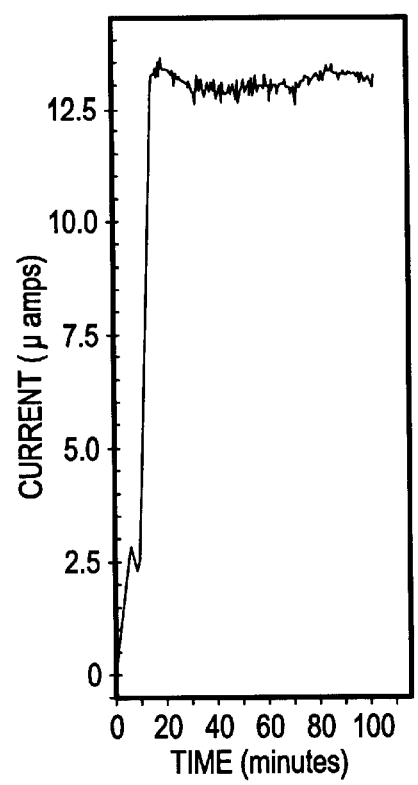
Figure 1C:
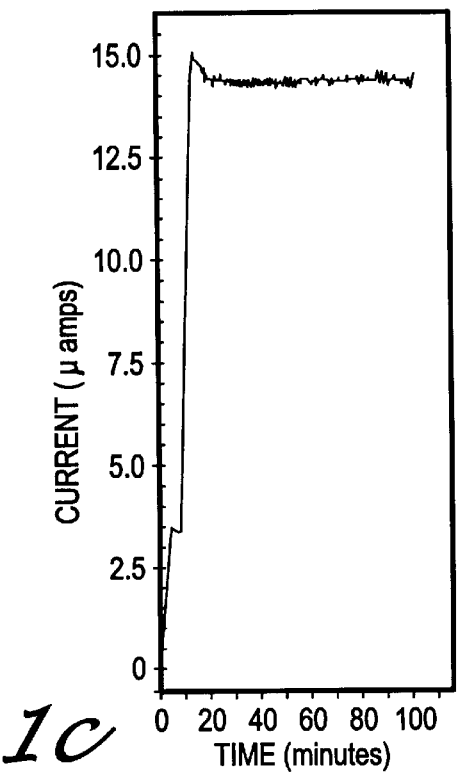

Results: FIGS. 1a to 1c show the current profiles of the capillary electrophoretic separations of DNA sequencing fragments from plasmid G2 template, with a) formamide as a loading solution, b) the disclosed branched polymer solution as a loading solution, or c) the commercial linear polymer as a loading solution. As shown in FIG. 1a, when formamide was used as a loading solution, the current profile started with a lower value of 7.3 µAmps (compared to FIGS. 1b and 1c) and then further decreased to about 3.5 µAmps at a separation time of 90 minutes. The clogging of the capillary with the injected large-sized template molecules caused the current instability. On the. other hand, when the disclosed branched polymer solution or the commercial linear polymer was used as a loading solution, the current profiles were quite stable, as shown in FIGS. 1b and 1c, indicating the effectiveness of the suppression of the entrance of template molecules into the capillary during the injection course.

Figure 2A:
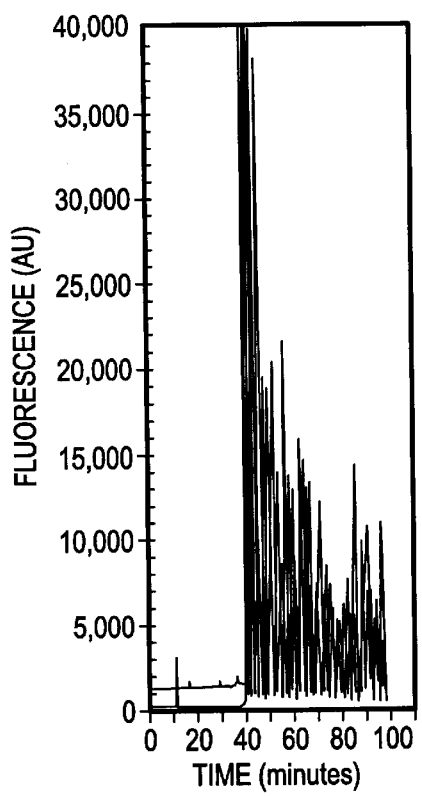
FIGS. 2(a) to 2(c) are electropherograms of DNA sequencing separations with the CEQ 2000 DNA Analysis System.
Figure 2B:
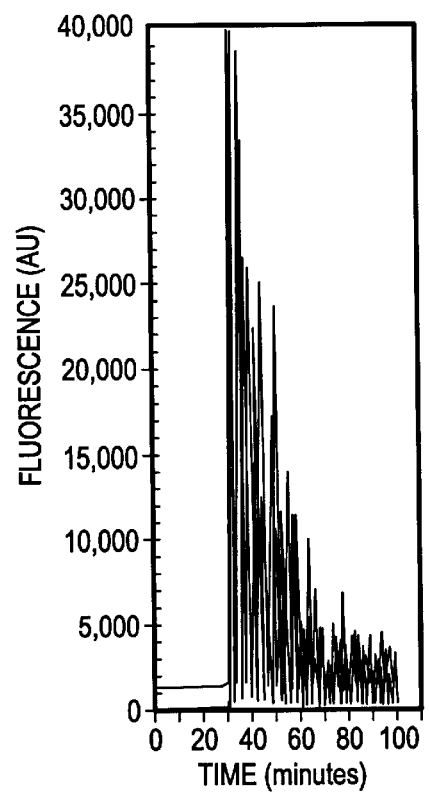
Figure 2C:
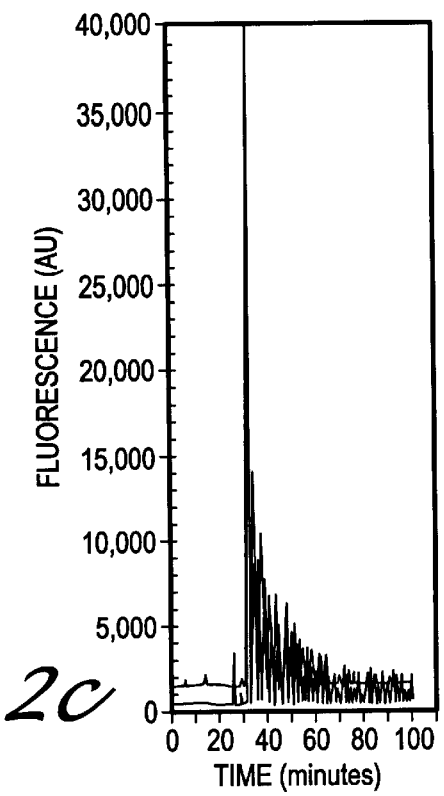

FIGS. 2a to 2c show the corresponding electropherograms of the capillary electrophoretic separations as described in FIGS. 1a to 1c. As shown in FIG. 2, the detection signal with the use of commercial linear polymer solution is significantly lower than the signal with the disclosed branched polymer solution or formamide. The reduced signal was caused by the partial entrapment of analyte DNA in the linear polymer solution, indicating the poorer capability of the linear polymer than the branched polymer to differentiate DNA based on size.

The performance of sequencing separations of the sequencing fragments of plasmid G2 template is shown in Table 1.

TABLE 1

| Loading Solution | % of Runs Passing the Base-Calling Accuracy* |
|---|---|
| Formamide | 25 |
| 1.25% branched PVP in formamide | 87.5 |
| 1.875% branched PVP in formamide | 87.5 |
| 2.5% branched PVP in formamide | 62.5 |
| Commercial linear polymer solution | 12.5 |

*The criteria for judging the base calling accuracy is based on the total number of errors of base calling for up to 500 bases. One run is defined as passed when the total number of errors is less than or equal to 10.

As shown in Table 1, there is significant improvement of the base calling quality with the use of the disclosed branched PVP solution of various concentrations, when compared to the use of formamide or the commercial linear polymer solution as a sample loading solution. The poor results of base calling accuracy with the commercial linear polymer solution are due to the reduced signal, as shown in FIG. 2c. Also, it is worth mentioning that the use of formamide as a loading solution could generate sufficient detection signal, compared to the branched PVP solution (see FIGS. 2a and b). However, the base calling quality with the former is poorer than the latter, due to the instability of the current with the use of formamide as a loading solution. The instability of the current inside the separation capillary reduces the electrophoretic mobility of the four-color sequencing fragments inside the capillary, leading to shorter sequencing readlength.

In addition, when dissolved in formamide with a concentration of 0.25% (w/v), the branched polymer with a molecular weight of about 10,000 daltons was also found to be effective in helping the current stability issue, as shown in Table 2.

TABLE 2

| | % of Runs with Stable Current Profile | |
|---|---|---|
| Loading Solution | pUC18 142 fmole + Delta 155 100 fmole | pUC18 600 fmole |
| Formamide | 50% | 0% |
| 0.25% branched PVP (Mw ≈ 10,000 Da) in formamide | 100% | 100% |
| Commercial linear polymer solution | 100% | 100% |

EXAMPLE 11

Separation of DNA Sequencing Fragments Generated from Various Preheated DNA Templates Using the Branched Polymer Solutions We also evaluated the applications of the branched PVP solution to the capillary electrophoretic separations of DNA sequencing fragments generated from various DNA templates which had been heated at either 80° C. for 3 min. or 96° C. for 1 min. prior to the sequencing reactions. The purpose of the pre-heating process is to randomly nick the DNA molecules, such that the super-coiled structures of DNA molecules can be relaxed and/or the closed-circular DNA molecules can be linearized, leading to better efficiency of DNA sequencing reaction. Table 2 shows the results with various DNA templates known to cause current problems, particularly at higher template concentrations.

TABLE 3

Percentages of Runs Passing Base Calling Accuracy*

| Sample Loading Solution Preheating Conditions | Formamide 96° C., 1 min in Water | 1.875% Branched PVD in Formamide 80° C., 3 min in Tris buffer | 1.875% Branched PVP in Formamide 96 C., 1 min in Tris buffer | Commercial Linear Polymer Solution No Preheat |
|---|---|---|---|---|
| G2 Template | | | | |
| 30 fmol | 0% | 100% | 100% | 75% |
| 50 fmol | 0% | 87.5% | 87.50% | 12.50% |
| 400 fmol | 62.50% | 50% | 62.50% | 62.50% |
| 1000 fmol | 12.50% | 25% | 100% | 75% |
| C3 Template | | | | |
| 30 fmol | 0% | 100% | 75% | 25% |
| 50 fmol | 0% | 87.50% | 87.50% | 37.50% |
| 400 fmol | 37.50% | 75% | 75% | 75% |
| 1000 fmol | 0% | 12.50% | 50% | 62.50% |
| PUC 18 Template | | | | |
| 30 fmol | 5 | 100.00% | 87.50% | 87.50% |
| 50 fmol | 0% | 75% | 50% | 25% |
| 400 fmol | 37.50% | 62.50% | 75% | 62.50% |
| 1000 fmol | 75% | 75% | 87.50% | 25% |
| Delta 155 Template | | | | |
| 30 fmol | 0% | 87.50% | 50% | 25% |
| 50 fmol | 12.50% | 50% | 100% | 100% |
| 150 fmol | 25% | 0% | 75% | 100% |
| 300 fmol | 0% | 0% | 37.50% | 25% |

*The criteria for judging the base calling accuracy is based on the number of total errors of base calling for up to 500 bases. One run is defined as passed when the total number of errors is less than or equal to 10.

As shown in Table 3, the use of branched PVP solution as a loading solution, in conjunction with a preheat treatment of DNA template, produces better results of base calling accuracy compared to the use of formamide or commercial linear polymer solution.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

References

1) Johnson, Ben F.; Menchen, Steven M.; Bloch, Will, U.S. Pat. No. 5,891,313, 1999.
2) Template Suppression Reagent, part #401674, The Perkin-Elmer Corp., Foster City, Calif.
3) "Principles of Polymerization", George Odian, 3rd Edition, p. 17, John Wiely & Sons, Inc., 1991.
4) "CEQ 2000 DNA Analysis System Performance", Nora M. Galvin et al., Technical Information #T-1854A, Beckman Coulter, Inc., 1998.

What is claimed is:

1. A method for preparing a sample containing biomolecule analytes and macrobiomolecules for capillary electrophoretic separation of the biomolecule analytes, the method comprising the steps of:
   (a) providing a reagent comprising a branched polymer capable of forming a polymer matrix that suppresses the injection of the macrobiomolecules into a capillary electrophoresis tube during electrokinetic injection of the biomolecule analytes; and
   (b) mixing the sample with an amount of the reagent sufficient to the injection of the macrobiomolecules contained in the sample into the capillary electrophoresis tube during electrokinetical injection of the biomolecule analytes contained in the sample,
   wherein said biomolecule analytes and said macrobiomolecules are nucleic acids.

2. The method of claim 1, wherein the branched polymer is selected from a group consisting of branched polyvinylpyrrolidone, and the like.

3. The method of claim 2, wherein the branched polymer is branched polyvinylpyrrolidone.

4. The method of claim 3, wherein the molecular weight of the branched polyvinylpyrrolidone is in a range of about 1,200,000 to 2,000,000 dalton.

5. The method of claim 1, wherein the reagent further comprises a solvent capable of dissolving the branched polymer for forming the polymer matrix.

6. The method of claim 5, wherein the concentration of the branched polymer is in a range of about 0.5% to 5% (w/v).

7. The method of claim 5, wherein the solvent is selected from a group consisting of formamide, and the like.

8. The method of claim 7, wherein the solvent is formamide.

9. The method of claim 1, wherein the macrobiomolecules are DNA sequencing templates.

10. The method of claim 1, wherein the biomolecule analytes are DNA fragments.

11. The method of claim 9, wherein the method further comprises a step of preheating the sample under a condition that nicks or linearizes the DNA sequencing templates.

12. The method of claim 11, wherein the sample is preheated at a temperature of above 80° C. for at least one minute.

13. A method of loading biomolecule analytes into a capillary electrophoresis tube from a sample containing the biomolecule analytes and macrobiomolecules, the method comprising the steps of:
   (a) providing a reagent comprising a branched polymer capable of forming a polymer matrix that suppresses the injection of the macrobiomolecules into a capillary electrophoresis tube during electrokinetic injection of the biomolecule analytes;
   (a) mixing the sample with an amount of the reagent to form a mixture;
   (b) electrokinetically injecting a portion of the mixture into the capillary electrophoresis tube;
   wherein the amount of the reagent is sufficient to suppress the injection of the macrobiomolecules into the capillary electrophoresis tube, and wherein said biomolecule analytes and said macrobiomolecules are nucleic acids.

14. The method of claim 13, wherein the branched polymer is selected from a group consisting of branched polyvinylpyrrolidone, and the like.

15. The method of claim 14, wherein the branched polymer is branched polyvinylpyrrolidone.

16. The method of claim 15, wherein the molecular weight of the branched polyvinylpyrrolidone is in a range of about 1,200,000 to 2,000,000 dalton.

17. The method of claim 13, wherein the reagent further comprises a solvent capable of dissolving the branched polymer for forming the polymer matrix.

18. The method of claim 17, wherein the solvent is selected from a group consisting of formamide, and the like.

19. The method of claim 18, wherein the solvent is formamide.

20. The method of claim 13, wherein the macrobiomolecules are DNA sequencing templates.

21. The method of claim 13, wherein the biomolecule analytes are DNA fragments.

22. The method of claim 20, wherein the method further comprises a step of preheating the sample under a condition that nicks or linearizes the DNA sequencing templates.

23. The method of claim 22, wherein the sample is preheated at a temperature of above 80° C. for at least one minute.

24. A sample loading reagent for loading biomolecule analytes contained in a sample into a capillary electrophoresis tube comprising:
   (a) a branched polymer capable of forming a polymer matrix that suppresses the injection of the macrobiomolecules into a capillary electrophoresis tube during electrokinetic injection of the biomolecule analytes, and
   (b) a solvent capable of dissolving the branched polymer for forming the polymer matrix,
   wherein said biomolecule analytes and said macrobiomolecules are nucleic acids, and wherein said branched polymer is selected from a group consisting of branched polyvinylpyrrolidone, homopolymer or copolymers of vinyl pyrrolidone, acrylamide and its derivatives, ethylene glycol, vinyl alcohol, celluloses and its derivatives, and mixtures thereof.

25. The sample loading reagent of claim 24, wherein the biomolecule analytes are DNA sequencing fragments.

26. The sample loading reagent of claim 24, wherein the branched polymer is selected from a group consisting of branched polyvinylpyrrolidone, and the like.

27. The sample loading reagent of claim 26, wherein the branched polymer is branched polyvinylpyrrolidone.

28. The sample loading reagent of claim 27, wherein the molecular weight of the branched polyvinylpyrrolidone is in a range of about 1,200,000 to 2,000,000 dalton.

29. The sample loading reagent of claim 24, wherein the solvent is selected from a group consisting of formamide, and the like.

30. The sample loading reagent of claim 29, wherein the solvent is formamide.

31. The sample loading of claim 24, wherein the concentration of the branched polymer is in a range of about 0.5 to 5% (w/v).

* * * * *

UNITED STATES PATENT AND TRADEMARK OFFICE
Certificate

Patent No. 6,294,064 B1                              Patented: September 25, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: M. Parameswara Reddy, Brea, CA (US); Tung-Liang Huang, Placentia, CA (US); Chitra K. Ratnayake, Yorba Linda, CA (US); Daniel A. Keys, Irvine, CA (US); and Mark Dobbs, Brea, CA (US).

Signed and Sealed this Eighteenth Day of July 2006.

GARY BENZION
*Supervisory Patent Examiner*
Art Unit 1637